(12) United States Patent
Morton et al.

(10) Patent No.: US 7,041,235 B2
(45) Date of Patent: May 9, 2006

(54) FLUORESCENT DIKETOPYRROLOPYRROLE ANALOGUES

(75) Inventors: Colin Morton, Basel (CH); David Macdonald Smith, Fife (GB); Abul Iqbal, Arconciel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 31 days.

(21) Appl. No.: 10/485,831

(22) PCT Filed: Aug. 1, 2002

(86) PCT No.: PCT/EP02/08590

§ 371 (c)(1),
(2), (4) Date: Feb. 4, 2004

(87) PCT Pub. No.: WO03/014255

PCT Pub. Date: Feb. 20, 2003

(65) Prior Publication Data

US 2004/0173777 A1   Sep. 9, 2004

(30) Foreign Application Priority Data

Aug. 10, 2001 (EP) ................... 01810773
Dec. 13, 2001 (EP) ................... 01811225

(51) Int. Cl.
C09K 11/06 (2006.01)
C09B 57/00 (2006.01)
C07D 487/04 (2006.01)
C08K 5/3415 (2006.01)

(52) U.S. Cl. ................... 252/301.16; 252/301.35; 252/301.34; 252/301.22; 252/301.21; 252/301.27; 546/276.7; 548/515; 548/452; 544/143; 544/333; 544/362

(58) Field of Classification Search ........... 252/301.16, 252/301.35, 301.34, 301.22, 301.21, 301.27; 546/276.7; 548/515, 452; 544/143, 333, 544/362

See application file for complete search history.

(56) References Cited

U.S. PATENT DOCUMENTS 5,616,725 A    4/1997  Zambounis et al. ........ 548/453
5,969,154 A *  10/1999 Hao et al. .................... 548/453
6,603,020 B1 * 8/2003  Moretti et al. ............... 548/453

OTHER PUBLICATIONS

Patent Abstracts of Japan Publication No. 03011357 (1991).

* cited by examiner

Primary Examiner—C. Melissa Koslow
(74) Attorney, Agent, or Firm—Joseph C. Suhadolnik

(57) ABSTRACT

The present invention relates to fluorescent diketopyrrolopyrrole analogues of the general formula (I), wherein $A^1$ and $A^2$ are $C_1-C_{18}$alkyl, $C_2-C_{18}$alkenyl, $C_2-C_{18}$alkynyl, $C_5-C_8$cycloalkyl, $C_5-C_8$cycloalkenyl, aryl or heteroaryl, $A^3$ and $A^4$ are independently of each other $C_1-C_{18}$alkyl, $Ar^3$, $-CR^{30}R^{31}-(CH_2)_m-Ar^3$, or $Y-R^{32}$, wherein $R^{30}$ and $R^{31}$ independently of each other stand for hydrogen or $C_1-C_4$alkyl, or phenyl which can be substituted up to three times with $C_1-C_3$alkyl, $Ar^3$ stands for aryl, in particular phenyl or 1- or 2-naphthyl, $C_5-C_8$cycloalkyl, in particular cyclohexyl, or heteroaryl, which can be substituted one to three times with $C_1-C_8$alkyl, $C_1-C_8$alkoxy, halogen or phenyl, which can be substituted with $C_1-C_8$alkyl or $C_1-C_8$alkoxy one to three times, and m stands for 0, 1, 2, 3 or 4, Y is C(O)— or $SO_2$— and $R^{32}$ is $C_1-C_{18}$alkyl, $Ar^3$, or aralkyl and $A^3$ can additionally be hydrogen, $C_1-C_8$alkyloxycarbonyl, such as tertbutoxycarbonyl, or aralkyloxycarbonyl, such as benzyloxycarbonyl, a process for their preparation and their use for the preparation of inks, colourants, pigmented plastics for coatings, non-impact printing material, colour filters, cosmetics, polymeric ink particles, toners, dye lasers and electroluminescent devices, or as fluorescent markers for immunoassays and fluorescent tracers for leak detection of fluids. The diketopyrrolopyrrole analogues of the general formula I show a high solid state fluorescence (I)

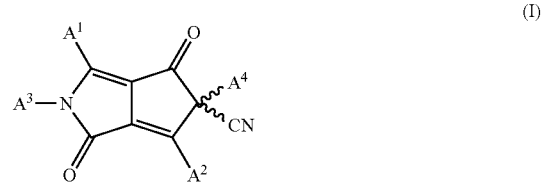

18 Claims, No Drawings

FLUORESCENT DIKETOPYRROLOPYRROLE ANALOGUES

The present invention relates to fluorescent diketopyrrolopyrrole analogues of the general formula I, a process for their preparation and their use for the preparation of inks, colourants, pigmented plastics for coatings, non-impact-printing material, colour filters, cosmetics, polymeric ink particles, toners, dye lasers and electroluminescent devices, or as fluorescent markers for immunoassays and fluorescent tracers for leak detection of fluids. The diketopyrrolopyrrole analogues of the general formula I show a high solid state fluorescence.

The object of this invention is to provide hew diketopyrrolopyrrole analogues which show high solid state fluorescence.

This object has surprisingly been solved by fluorescent diketopyrrolopyrrole analogues of the general formula

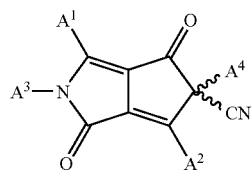

(I)

wherein $A^1$ and $A^2$ are $C_1$–$C_{18}$alkyl, $C_2$–$C_{18}$alkenyl, $C_2$–$C_{18}$alkynyl, $C_5$–$C_8$cycloalkyl $C_5$–$C_8$cycloalkenyl, aryl or heteroaryl, in particular radicals of the formula

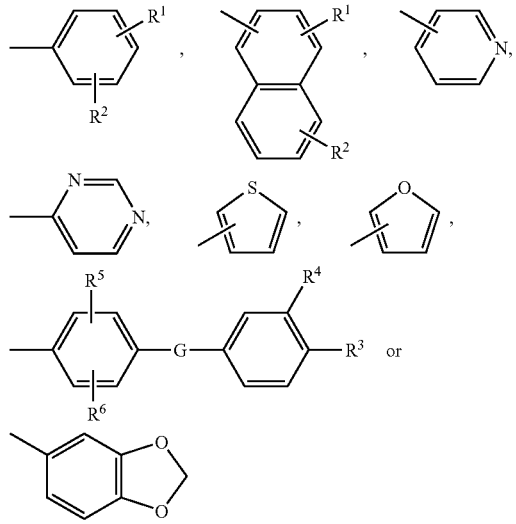

wherein
$R^1$ and $R^2$ are independently of each other hydrogen, halogen, $C_1$–$C_{18}$alkyl, $C_1$–$C_{18}$alkoxy, $C_1$–$C_{18}$alkylmercapto, amino, $C_1$–$C_{18}$alkylamino, di($C_1$–$C_{18}$alkyl)amino, $C_1$–$C_{18}$alkoxycarbonyl, $C_1$–$C_{18}$alkylaminocarbonyl, —CN, —NO$_2$, trifluoromethyl, $C_5$–$C_8$cycloalkyl, —CH=N—($C_1$–$C_{18}$alkyl),

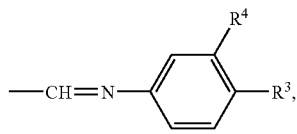

phenyl, imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$—, —CONH— or —NR$^7$—, $R^3$ and $R^4$ are independently of each other hydrogen, halogen, $C_1$–$C_6$alkyl, $C_1$–$C_{18}$alkoxy or —CN, $R^5$ and $R^6$ are independently of each other hydrogen, halogen or $C_1$–$C_6$alkyl, and $R^7$ is hydrogen or $C_1$–$C_6$alkyl, $A^3$ and $A^4$ are independently of each other $C_1$–$C_{18}$alkyl, Ar$^3$, —CR$^{30}$R$^{31}$—(CH$_2$)$_m$—Ar$^3$, or Y—R$^{32}$, wherein $R^{30}$ and $R^{31}$ independently of each other stand for hydrogen or $C_1$–$C_4$alkyl, or phenyl which can be substituted up to three times with $C_1$–$C_3$alkyl, Ar$^3$ stands for aryl, in particular phenyl or 1- or 2-naphthyl, $C_5$–$C_8$cycloalkyl, in particular cyclohexyl, or heteroaryl, which can be substituted one to three times with $C_1$–$C_8$alkyl, $C_1$–$C_8$alkoxy, halogen or phenyl, which can be substituted with $C_1$–$C_8$alkyl or $C_1$–$C_8$alkoxy one to three times, and m stands for 0, 1, 2, 3 or 4, Y is —C(O)— or —SO$_2$— and $R^{32}$ is $C_1$–$C_{18}$alkyl, Ar$^3$, or aralkyl and $A^3$ can additionally be hydrogen, $C_1$–$C_8$alkyloxycarbonyl, such as tert-butoxycarbonyl, or aralkyloxycarbonyl, such as benzyloxycarbonyl.

The residues $A^1$ and $A^2$ are in general selected from $C_1$–$C_{18}$alkyl, $C_2$–$C_{18}$alkenyl, $C_2$–$C_{18}$alkynyl, $C_5$–$C_8$cycloalkyl, such as cyclopentyl, cyclohexyl, cycloheptyl and cyclooctyl, in particular cyclohexyl, $C_5$–$C_8$cycloalkenyl, such as cyclopentenyl, cyclopentadienyl and cyclohexenyl, in particular cyclohex-3-enyl, aryl and heteroaryl. Diketopyrrolopyrrole analogues, wherein $A^1$ and $A^2$ are radicals of the formula

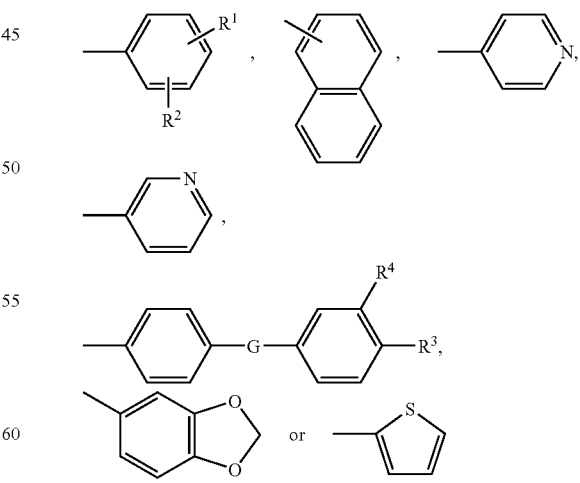

wherein $R^1$ and $R^2$ are independently of each other hydrogen, fluoro, chloro, bromo, $C_1$–$C_4$alkyl, $C_1$–$C_6$alkoxy, amino, $C_1$–$C_6$alkylamino, di($C_1$–$C_6$alkyl)amino, phenyl or CN, G is —O—, —NR$^7$—, —N=N— or —SO$_2$—, R$^3$ and R$^4$ are hydrogen, and R$^7$ is hydrogen, methyl or ethyl are preferred and diketopyrrolopyrrole analogues, wherein A$^1$ and A$^2$ are radicals of the formula

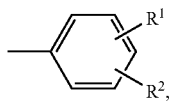

wherein R$^1$ and R$^2$ are independently of each other hydrogen, C$_1$–C$_4$alkyl, such as methyl, or tert-butyl, halogen, such as fluoro, chloro, or bromo, di(C$_1$–C$_4$alkyl)amino, such as dimethylamino, phenyl or CN, are particularly preferred.

In general A$^3$ and A$^4$ are independently of each other C$_1$–C$_{18}$alkyl, Ar$^3$, —CR$^{30}$R$^{31}$—(CH$_2$)$_m$—Ar$^3$, —C(O)—R$^{32}$ or Y—R$^{32}$, wherein R$^{30}$ and R$^{31}$ independently of each other stand for hydrogen or C$_1$–C$_4$alkyl, or phenyl which can be substituted up to three times with C$_1$–C$_3$alkyl, wherein Ar$^3$ stands for aryl, in particular phenyl or 1- or 2-naphthyl, C$_5$–C$_8$cycloalkyl, such as cyclopentyl, cyclohexyl, cycloheptyl and cyclooctyl, in particular cyclohexyl, or heteroaryl, which can be substituted one to three times with C$_1$–C$_8$alkyl, C$_1$–C$_8$alkoxy, halogen or phenyl, which can be substituted with C$_1$–C$_8$alkyl or C$_1$–C$_8$alkoxy one to three times, and m stands for 0, 1, 2, 3 or 4, Y is —C(O)— or —SO$_2$— and R$^{32}$ is C$_1$–C$_{18}$alkyl, Ar$^3$, or aralkyl, wherein A$^3$ can additionally be hydrogen, C$_1$–C$_8$alkyloxycarbonyl, such as tert-butoxycarbonyl, or aralkyloxycarbonyl, such as benzyloxycarbonyl.

The residues A$^3$ and A$^4$ are preferably selected from C$_1$–C$_8$alkyl such as methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl, in particular C$_1$–C$_4$alkyl, such as methyl, ethyl, n-propyl, isopropyl, n-butyl, sec.-butyl, isobutyl or tert.-butyl, Y—R$^{32}$ wherein Y is —C(O)— and R$^{32}$ is

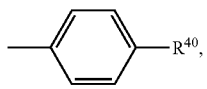

wherein R$^{40}$ is hydrogen, C$_1$–C$_4$alkyl, —O—C$_1$–C$_4$alkyl, —S—C$_1$–C$_4$alkyl or —(CH$_2$)$_m$—Ar wherein m is 0 or 1 and Ar is a group of the formula

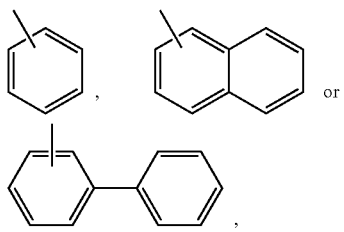

which can be substituted one to three times with C$_1$–C$_8$alkyl, C$_1$–C$_8$alkoxy, halogen or phenyl.

Examples of preferred residues Ar are

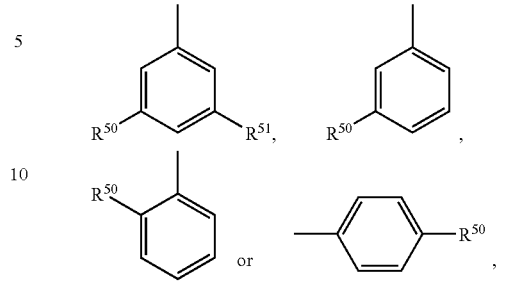

wherein R$^{50}$ and R$^{51}$ are independently of each other methyl, ethyl, n-propyl, isopropyl, n-butyl, sec.-butyl, isobutyl, tert.-butyl, methoxy, ethoxy, isopropoxy, tert.-butoxy or chlorine.

C$_1$–C$_{18}$alkyl is typically linear or branched—where possible—and examples of C$_1$–C$_{18}$alkyl are methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl and octadecyl. C$_1$–C$_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl is preferred. C$_1$–C$_4$alkyl such as methyl, ethyl, n-propyl, isopropyl, n-butyl, sec.-butyl, isobutyl or tert.-butyl is particularly preferred. The term "C$_2$–C$_{18}$alkenyl group" means an unsaturated linear or branched aliphatic hydrocarbon group containing one or more double bonds, in particular C$_{2-8}$-alkenyl, such as vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl and 1,4-pentadien-3-yl. The term "C$_2$–C$_{18}$alkynyl group" means an unsaturated aliphatic hydrocarbon group containing a triple bond, in particular C$_2$–C$_8$-alkynyl such as ethynyl, 1-propyn-1-yl, 2-butyn-1-yl, 3-butyn-1-yl, 2-pentyn-1-yl and 3-pentyn-2-yl.

Examples of C$_1$–C$_{18}$alkoxy, which can be linear or branched, are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, wherein C$_1$–C$_4$alkoxy such as methoxy, ethoxy, n-propoxy, isopropoxy, n-butoxy, sec.-butoxy, isobutoxy and tert.-butoxy is preferred. Examples of C$_1$–C$_{18}$alkylmercapto are the same groups as mentioned for the alkoxy groups, except that the oxygen atom of the ether linkage is replaced by a sulfur atom. Examples and preferences for C$_1$–C$_{18}$alkyl in C$_1$–C$_{18}$alkylamino and C$_1$–C$_{18}$alkylaminocarbonyl are the same as mentioned for C$_1$–C$_{18}$alkyl. Examples and preferences for C$_1$–C$_{18}$alkoxy in C$_1$–C$_{18}$alkoxycarbonyl are the same as mentioned for C$_1$–C$_{18}$alkoxy.

The term "aryl group" is typically C$_6$–C$_{24}$aryl, such as phenyl, 1-naphthyl, 2-naphthyl, 4-biphenylyl, phenanthryl, terphenylyl, pyrenyl, 2- or 9-fluorenyl or anthracenyl, preferably C$_6$–C$_{12}$aryl such as phenyl, 1-naphthyl, 2-naphthyl, 4-biphenylyl, which may be unsubstituted or substituted.

In case of $A^1$ and $A^2$ the term "aryl" also includes the following residues:

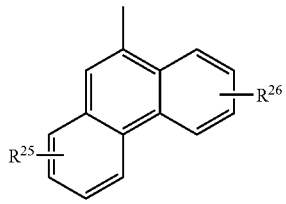

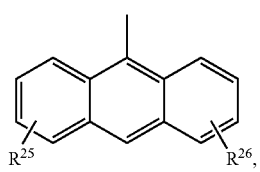

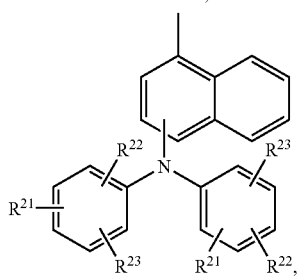

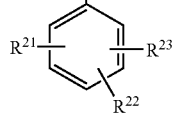

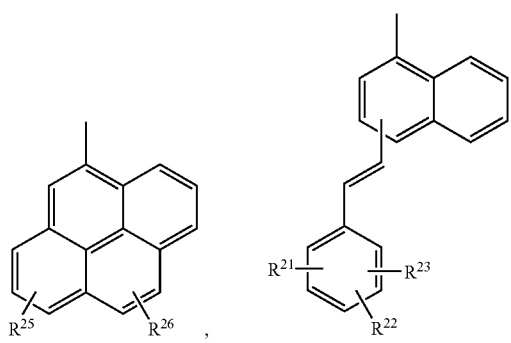

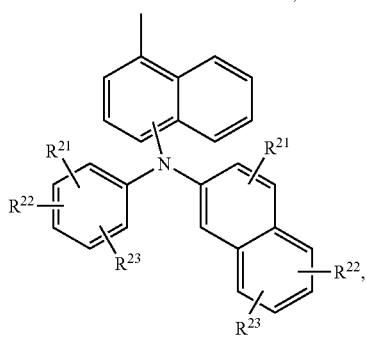

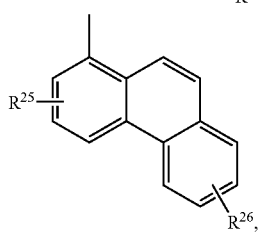

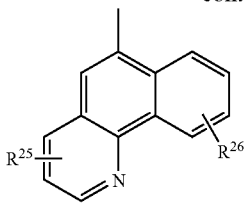

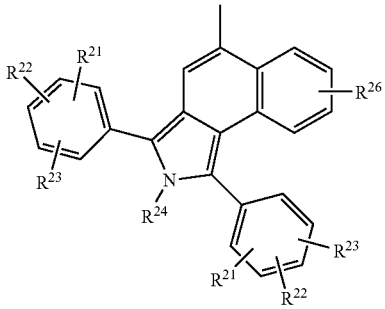

wherein $R^{21}$, $R^{22}$, $R^{23}$, $R^{25}$ and $R^{26}$ are independently of each other hydrogen, $C_1$–$C_8$alkyl, a hydroxyl group, a mercapto group, $C_1$–$C_8$alkoxy, $C_1$–$C_8$alkylthio, halogen, halo-$C_1$–$C_8$alkyl, a cyano group, an aldehyde group, a ketone group, a carboxyl group, an ester group, a carbamoyl group, an amino group, a nitro group, a silyl group or a siloxanyl group and $R^{24}$ is a $C_1$–$C_6$alkyl group. Preferably $R^{21}$, $R^{22}$, $R^{23}$, $R^{25}$ and $R^{26}$ are independently of each other hydrogen, $C_1$–$C_8$alkyl, $C_1$–$C_8$alkoxy or $C_1$–$C_8$alkylthio, wherein the following residues are particularly preferred:

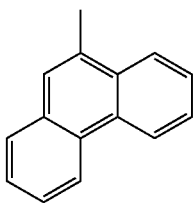

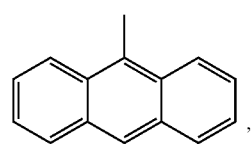

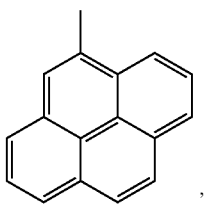

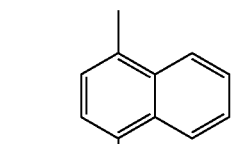

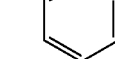

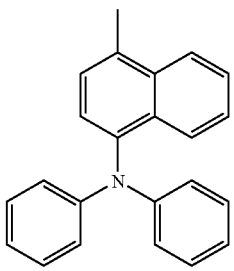

-continued

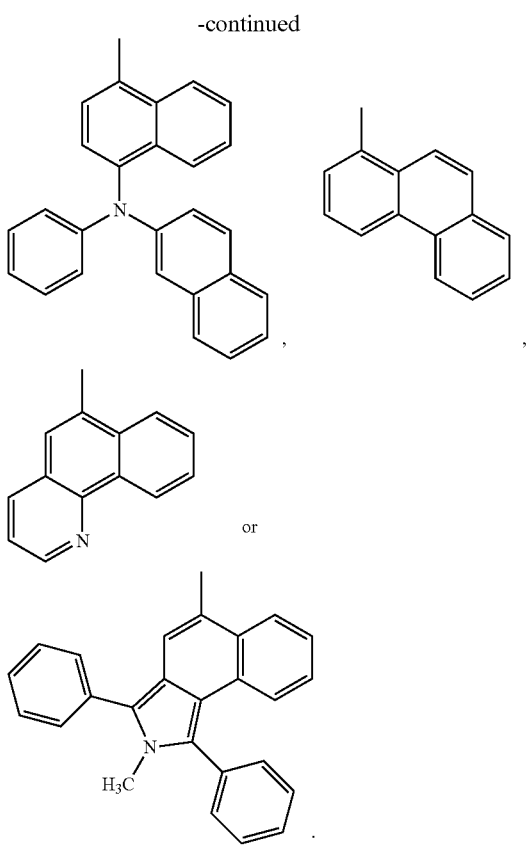

The term "aralkyl group" is typically $C_7$–$C_{24}$aralkyl, such as benzyl, 2-benzyl-2-propyl, β-phenylethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$–$C_{18}$aralkyl such as benzyl, 2-benzyl-2-propyl, β-phenyl-ethyl, α,α-dimethylbenzyl, ω-phenyl-butyl, ω,ω-dimethyl-ω-(phenylbutyl, ω-phenyldodecyl or ω-phenyloctadecyl, and particularly preferred $C_7$–$C_{12}$aralkyl such as benzyl, 2-benzyl-2-propyl, β-phenylethyl, α,α-dimethylbenzyl, ω-phenylbutyl, or ω,ω-dimethyl-ω-phenylbutyl, in which both the aliphatic hydrocarbon group and aromatic hydrocarbon group may be unsubstituted or substituted.

Examples of $C_5$–$C_8$cycloalkyl are cyclopentyl, cyclohexyl, cycloheptyl and cyclooctyl, which may be unsubstituted or substituted. The term "$C_5$–$C_8$cycloalkenyl group" means an unsaturated alicyclic hydrocarbon group containing one or more double bonds, such as cyclopentenyl, cyclopentadienyl and cyclohexenyl, which may be unsubstituted or substituted.

The term "heteroaryl" is a ring with five to seven ring atoms, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl.

$C_1$–$C_{18}$alkyl in $C_1$–$C_{18}$alkylamino and di($C_1$–$C_{18}$alkyl)amino are as defined above. Examples of $C_1$–$C_{18}$alkylamino and di($C_1$–$C_{18}$alkyl)amino are dimethylamino, diethylamino, methylethylamino, methylpropylamino, dibutylamino and hydroxyethylmethylamino.

Examples of a halogen atom are fluorine, chlorine, bromine and iodine.

If the above-mentioned substituents can be substituted, possible substituents are $C_1$–$C_8$alkyl, a hydroxyl group, a mercapto group, $C_1$–$C_8$alkoxy, $C_1$–$C_8$alkylthio, halogen, halo-$C_1$–$C_8$alkyl, a cyano group, an aldehyde group, a ketone group, a carboxyl group, an ester group, a carbamoyl group, an amino group, a nitro group, a silyl group or a siloxanyl group, The present application is also directed to a process for the preparation of the fluorescent diketopyrrolopyrrole analogues of the general formula

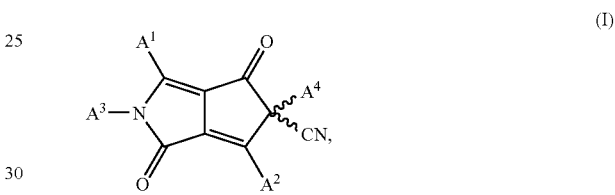

(I)

reacting a compound of the general formula

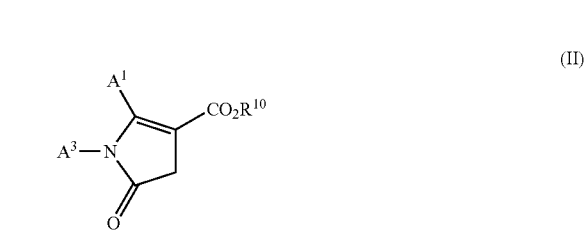

(II)

with a compound of the general formula

(III)

in the presence of a base and reacting the obtained Intermediate of the formula

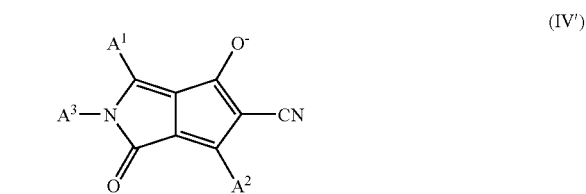

(IV')

with a compound of the general formula $$A^4—X \quad (V),$$

wherein $A^1$, $A^2$, $A^3$ and $A^4$ have the meanings as given above, $R^{10}$ is $C_1$–$C_{18}$alkyl, in particular $C_1$–$C_4$alkyl, aryl, in particular phenyl, or aralkyl, in particular benzyl, which can be substituted one to three times with $C_1$–$C_8$alkyl, $C_1$–$C_8$alkoxy, or halogen and X is a leaving group.

Hence, the present invention also relates to diketopyrrolopyrrole analogues of the general formula

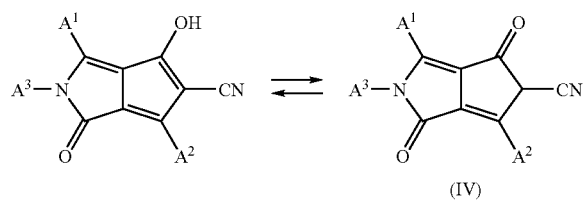

(IV)

wherein $A^1$, $A^2$ and $A^3$ have the meanings as given above, which could exist in both tautomeric forms and are intermediates in the process for the preparation of the diketopyrrolopyrrole analogues of the general formula I.

The compounds of the formula II are commercially available or can be prepared in analogy to known methods (see, for example, U.S. Pat. Nos. 4,749,795 and 4,778,899), for example by reacting a β-carbonyl ester compound with an α-bromo carboxylic ester in a solvent, like acetone, 1,2-dimethoxyethane or a mixture thereof, in the presence of a base, like potassium carbonate, to obtain a diester which in turn is reacted with $A^3NH_3$:

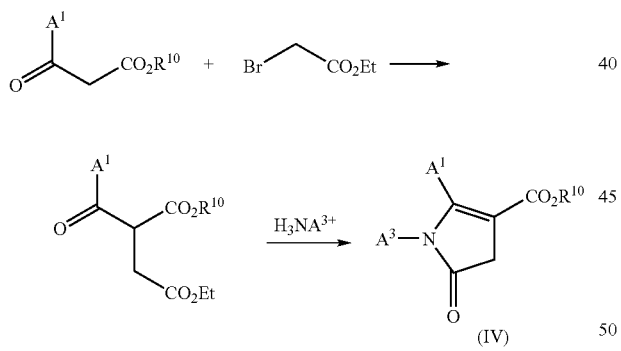

wherein $A^1$, $A^3$ and $R^{10}$ have the meanings as given above, wherein $A^3$ is preferably hydrogen; or by a copper catalyzed decomposition of diazoacetates in the presence of enaminoamides (G. Maas, A. Müller, J. prakt. Chem. 340 (1998) 315–322):

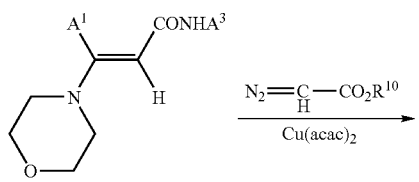

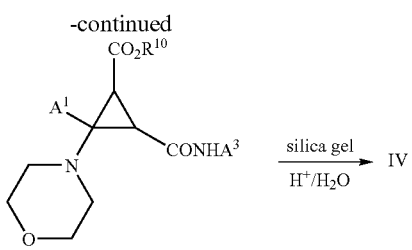

wherein $A^1$, $A^3$ and $R^{10}$ have the meanings as given above, wherein $A^3$ is preferably aryl, in particular phenyl or substituted phenyl.

The compounds of the formula III, which are employed as E isomer, Z isomer or a mixture of E and Z isomers, are commercially available or can be prepared in analogy to known methods, for example by adapting a conventional Horner-Wadsworth-Emmons-Reaction (see W. S. Wadsworth, Org. React. 25 (1977) 75).

The process of the present invention can be carried out as two step synthesis or as one-pot synthesis.

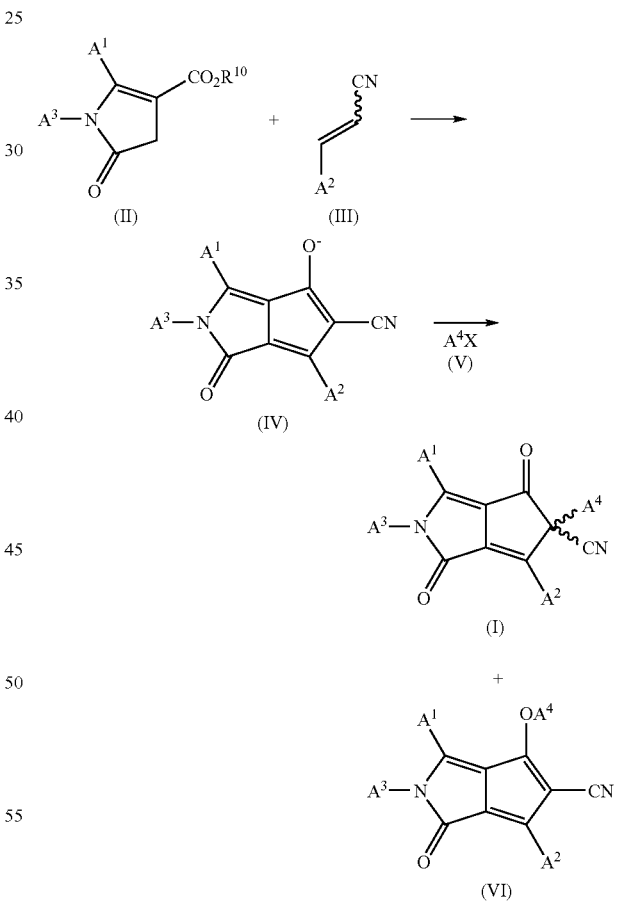

wherein $A^3$ in formula I or formula VI is the same as $A^4$ if $A^3$ in formula IV is hydrogen.

In case of the two step synthesis in a first step the lactam ester of the general formula II is reacted with the cyano compound of formula (III) in the presence of a base, such as sodium ′amylate, in an organic solvent, such as ′amyl alcohol, at a temperature of 20° C. to the reflux temperature of the solvent for a time of 0.5 to 48 hours, wherein the reaction conditions can vary depending on the starting materials and the reagents employed.

In a second step the obtained intermediate of the general formula (IV) is reacted with an electrophile of the general formula (V) in the presence of a base, such as sodium ′amylate, in an organic solvent, such as ′amyl alcohol, at a temperature of 20° C. to the reflux temperature of the solvent for a time of 0.5 to 240 hours to obtain the desired compound of the general formula (I), wherein the reaction conditions can vary depending on the starting materials and the reagents employed.

In case of the one pot synthesis the lactam ester of the general formula II is reacted with the cyano compound of formula (III) in the presence of a base, such as sodium ′amylate, in an organic solvent, such as ′amyl alcohol, at a temperature of 20° C. to the reflux temperature of the solvent for a time of 0.5 to 48 hours, and the intermediate of the general formula (IV') prepared in situ is directly reacted with the electrophile of the general formula (V) at a temperature of 20° C. to the reflux temperature of the solvent for a time of 0.5 to 240 hours to obtain the desired compound of the general formula (I), wherein the reaction conditions can vary depending on the starting materials and the reagents employed.

Depending on the electrophile $A^4X$, the starting materials, the reagents, the solvents and the reaction conditions the compounds of the general formula (I), the compounds of the general formula (VI) or a mixture of the compounds of the general formula (I) and (VI) are obtained by the process of the present invention. If the electrophile is, for example, a soft electrophile, like methyl or ethyl iodide, the compounds of the general formula (I) are the main product, whereas, if the electrophile is a hard eletrophile, like methyl or ethyl tosylate, the compounds of the general formula (VI) are the main product.

Consequently, the term "leaving group" means preferably a group which imparts a soft nature to the electrophile, such as iodine, bromine or chlorine.

Compounds of the formula I, wherein $A^3$ is $A^4$, can be prepared by reacting compounds of the formula IV or IV', wherein $A^3$ is hydrogen, with two equivalents of the electrophile $A^4X$. Compounds of the formula I, wherein $A^3$ is different from $A^4$, can be prepared by using compounds of the formula II as starting material, wherein $A^3$ is different from hydrogen, or by using the fact that at first the carbon atom and then the nitrogen atom is attacked by the electrophile $A^4X$, or the nitrogen atom can be reacted with a protecting group, for example by reacting a compound of the general formula (IV) or (IV') with a base, like lithium diisopropylamide, and a protecting group, like Boc, reacting the obtained product with a first electropile $A^4X$, optionally removing the protecting group and reacting the obtained compound with a second electrophile $A^3X$.

The present invention relates also to the use of the inventive DPP analogues of the general formula I for the preparation of inks for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fibre tips, card, wood, (wood) stains, metal, inking pads or inks for impact printing processes (with impact-pressure ink ribbons), for the preparation of colourants for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of colour filters, especially for visible light in the range from 400 to 700 nm, for liquid-crystal displays (LCDs) or charge combined devices (CCDs) or for the preparation of cosmetics or for the preparation of polymeric ink particles, toners, dye lasers, dry copy toners liquid copy toners, or electrophotographic toners, and electroluminescent devices.

Illustrative examples of suitable organic materials of high molecular weight which can be coloured with the inventive fluorescent DPP analogues of the general formula I are vinyl polymers, for example polystyrene, poly-α-methylstyrene, poly-p-methylstyrene, poly-p-hydroxystyrene, poly-p-hydroxyphenylstyrene, polymethyl methacrylate and polyacrylamide as well as the corresponding methacrylic compounds, polymethyl maleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers which are derived from maleimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylene sulfides; polyepoxides; polyolefins such as polyethylene and polypropylene; polyalkadienes; biopolymers and the derivatives thereof e.g. cellulose, cellulose ethers and esters such as ethylcellulose, nitrocellulose, cellulose acetate and cellulose butyrate, starch, chitin, chitosan, gelatin, zein; natural resins; synthetic resins such as alkyd resins, acrylic resins, phenolic resins, epoxide resins, aminoformaldehyde resins such as urea/formaldehyde resins and melamine/formaldehyde resin; vulcanized rubber; casein; silicone and silicone resins; rubber, chlorinated rubber; and also polymers which are used, for example, as binders in paint systems, such as novolaks which are derived from $C_1$–$C_6$-aldehydes such as formaldehyde and acetaldehyde and a binuclear or mononuclear, preferably mononuclear, phenol which, if desired, is substituted by one or two $C_1$–$C_9$alkyl groups, one or two halogen atoms or one phenyl ring, such as o-, m- or p-cresol, xylene, p-tert.-butylphenol, o-, m- or p-nonylphenol, p-chlorophenol or p-phenylphenol, or a compound having more than one phenolic group such as resorcinol, bis(4-hydroxyphenyl)methane or 2,2-bis(4-hydroxyphenyl)propane; as well as suitable mixtures of said materials.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic materials may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the inventive fluorescent DPP analogues of the general formula I are used for the mass colouration of polyvinyl chloride, polyamides and, especially, polyolefins such as polyethylene and polypropylene as well as for the preparation of paint systems, including powder coatings, inks, printing inks, colour filters and coating colours. Illustrative examples of preferred binders for paint systems are alkyd/melamine resin paints, acryl/melamine resin paints, cellulose acetate/cellulose butyrate paints and two-pack system lacquers based on acrylic resins which are crosslinkable with polyisocyanate.

According to observations made to date, the inventive fluorescent DPP analogues of the general formula I can be added in any desired amount to the material to be coloured, depending on the end use requirements. In the case of high molecular weight organic materials, for example, the fluorescent DPP analogues of the general formula I prepared according to this invention can be used in an amount in the range from 0.01 to 50, preferably from 0.01 to 5% by weight, based on the total weight of the coloured high molecular weight organic material.

Hence, another embodiment of the present invention relates to a composition comprising
(a) 0.01 to 50, preferably 0.01 to 5, particularly preferred 0.01 to 2% by weight, based on the total weight of the coloured high molecular organic material, of a fluorescent DPP analogue of the general formula I according to the present invention, and
(b) 99.99 to 50, preferably 99.99 to 95, particularly preferred 99.99 to 98% by weight, based on the total weight of the coloured high molecular organic material, of a high molecular organic material, and
(c) if desired, customary additives such as rheology improvers, dispersants, fillers, paint auxiliaries, siccatives, plasticizers, UV-stabilizers, and/or additional pigments or corresponding precursors in effective amounts, such as e.g. from 0 to 50% by weight, based on the total weight of (a) and (b).

To obtain different shades, the inventive fluorescent DPP analogues of the general formula I may advantageously be used in admixture with fillers, transparent and opaque white, coloured and/or black pigments as well as customary lustre pigments in the desired amount.

For the preparation of paint systems, coating materials, colour filters, inks and printing inks, the corresponding high molecular weight organic materials, such as binders, synthetic resin dispersions etc. and the inventive fluorescent DPP analogues of the general formula I are usually dispersed or dissolved together, if desired together with customary additives such as dispersants, fillers, paint auxiliaries, siccatives, plasticizers and/or additional pigments or pigment precursors, in a common solvent or mixture of solvents. This can be achieved by dispersing or dissolving the individual components by themselves, or also several components together, and only then bringing all components together, or by adding everything together at once.

Hence, a further embodiment of the present invention relates to a method of using the inventive fluorescent DPP analogues of the general formula I for the preparation of dispersions and the corresponding dispersions, and paint systems, coating materials, colour filters, inks and printing inks comprising the inventive fluorescent DPP analogues of the general formula I.

A particularly preferred embodiment relates to the use of the inventive DPPs I for the preparation of fluorescent tracers for e.g. leak detection of fluids such as lubricants, cooling systems etc., as well as to fluorescent tracers or lubricants comprising the inventive DPP analogues of the general formula I. Usually, such lubricant compositions, e.g. for a refrigerant, comprise an oil selected from the group consisting of naphthalenic oils, paraffinic oils, alkylated benzene oils, polyalkyl silicate oils, polyglycols, esters, polyether polyols, polyvinyl ethers, polycarbonates, fluorinated silicones, perfluoroethers, aromatic compounds with fluoroalkyloxy or fluoroalkylthio substituents. The amount of the inventive DPP analogue of the general formula I in the lubricant is chosen generally in an amount of from 100 to 1000 ppm. If the inventive compound I is water-soluble, it could be used as tracer in water as well.

A particular embodiment of this invention concerns ink jet inks comprising the inventive fluorescent DPP analogues of the general formula I.

For the colouring of high molecular weight organic material, the inventive DPP analogues of the general formula I, optionally in the form of masterbatches, usually are mixed with the high molecular weight organic materials using roll mills, mixing apparatus or grinding apparatus. Generally, the pigmented material is subsequently brought into the desired final form by conventional processes, such as calandering, compression molding, extrusion, spreading, casting or injection molding. In order to prepare non-rigid moldings or to reduce their brittleness it is often desired to incorporate so-called plasticizers into the high molecular weight organic materials prior to forming. Examples of compounds which can be used as such plasticizers are esters of phosphoric acid, phthalic acid or sebacic acid. The plasticizers can be added before or after the incorporation of the inventive DPP analogues of the general formula I into the polymers. It is also possible, in order to achieve different hues, to add fillers or other colouring constituents such as white, colour or black pigments in desired amounts to the high molecular weight organic materials in addition to the inventive DPP analogues of the general formula I.

For colouring lacquers, coating materials and printing inks the high molecular weight organic materials and the inventive DPP analogues of the general formula I, alone or together with additives, such as fillers, other pigments, siccatives or plasticizers, are generally dissolved or dispersed in a common organic solvent or solvent mixture. In this case it is possible to adopt a procedure whereby the individual components are dispersed or dissolved individually or else two or more are dispersed or dissolved together and only then are all of the components combined.

The present invention additionally relates to inks comprising a colouristically effective amount of the inventive DPP analogue of the general formula I.

Processes for producing inks especially for ink jet printing are generally known and are described for example in U.S. Pat. No. 5,106,412.

When mixing a DPP analogue of the general formula I with polymeric dispersants it is preferred to use a water-dilutable organic solvent.

The weight ratio of the pigment dispersion to the ink in general is chosen in the range of from 0.001 to 75% by weight, preferably from 0.01 to 50% by weight, based on the overall weight of the ink.

The preparation and use of colour filters or colour-pigmented high molecular weight organic materials are well-known in the art and described e.g. in Displays 14/2, 1151 (1993), EP-A-784085, or GB-A-2,310,072.

The colour filters can be coated for example using inks, especially printing inks, which can comprise the inventive DPPs of the general formula I or can be prepared for example by mixing a DPP analogue of the general formula I with chemically, thermally or photolytically structurable high molecular weight organic material (so-called resist). The subsequent preparation can be carried out, for example, in analogy to EP-A-654 711 by application to a substrate, such as a LCD, subsequent photostructuring and development.

The present invention relates, moreover, to toners comprising a DPP analogue of the general formula I or a high molecular weight organic material coloured with a DPP analogue of the general formula I in a colouristically effective amount.

In a particular embodiment of the process of the invention, toners, coating materials, inks or coloured plastics are prepared by processing masterbatches of toners, coating materials, inks or coloured plastics in roll mills, mixing apparatus or grinding apparatus.

The present invention additionally relates to colourants, coloured plastics, polymeric ink particles, or non-impact-printing material comprising an inventive DPP analogue of the general formula I or a high molecular weight organic material coloured with a DPP analogue of the general formula I in a colouristically effective amount.

A colouristically effective amount of the pigment dispersion according to this invention comprising an inventive DPP I denotes in general from 0.0001 to 99.99% by weight, preferably from 0.001 to 50% by weight and, with particular preference, from 0.01 to 5% by weight, based on the overall weight of the material pigmented therewith.

Further, the inventive compounds I can be used for textile application and for the dyeing of paper.

The following examples illustrate various embodiments of the invention, but the scope of the invention is not limited thereto.

EXAMPLES $^1$H NMR spectra were obtained at 300 MHz for solutions in $d_6$-dimethyl sulfoxide. Chemical shifts (δ) are expressed relative to $Si(CH_3)_4$ and coupling constants (J) in Hz.

Example 1

5-Cyano-N,5-dimethyl-3,6-diphenyl-cyclopenta[c]pyrrole-1,4-dione 1d

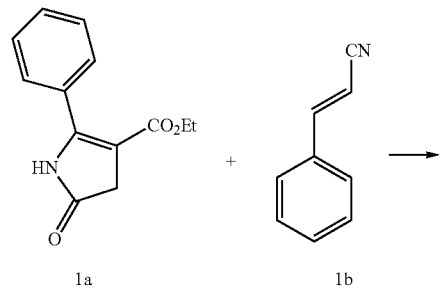

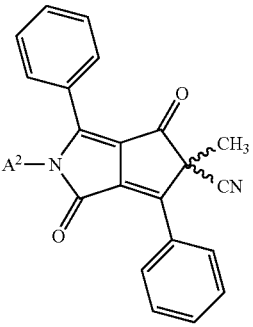

1d [$A^3$ = $CH_3$ (Example 1)]
1o [$A^3$ = H (Example 10)]

To 2-methyl-2-butanol (300 ml) is added sodium (10.10 g, 0.439 mol) with stirring under nitrogen and the mixture is heated to reflux (105–110° C.) until all the sodium is dissolved. The mixture is cooled to 80° C. then compounds 1a (51.0 g, 0.221 mol) and 1b (31.4 g, 0.249 mol) are added. The mixture is heated to reflux for 16 h, then cooled slowly to room temperature. Methyl iodide (626.60 g, 4.42 mol) is added and the mixture is heated to 40° C. for 66 h. The mixture is cooled to room temperature and acidified slowly with dilute hydrochloric acid. The organic extracts are washed with water, dried ($MgSO_4$) and concentrated. Flash chromatography on silica gel H (Fluka, 5–40 μm particle size) eluted with hexane/ethyl acetate yields the fluorescent orange solid 1d. Yield 3.11 g, 4%, m.p. (as determined by differential scanning calorimetry) 199–200° C. $\delta_H$ 1.87 (3H, s, $CCH_3$), 3.32 (3H, s, $NCH_3$), 7.61–7.64 (6H, m, m-Ip-Ar—H), 7.83–7.87 (2H, m, o- Ar—H adjacent to N—$CH_3$), 8.50–8.53 (2H, o- Ar—H adjacent to $CCH_3$). v/cm$^{-1}$ 2195 (C≡N), 1694 (C=O), 1655 (C=O).

| Elemental analysis: | C | H | N |
|---|---|---|---|
| calculated | 77.6% | 4.7% | 8.2% |
| observed | 77.3% | 4.6% | 7.9% |

Example 2

3-(4'-Chlorophenyl)-5-cyano-N,5-dimethyl-6-phenyl-cyclopenta[c]pyrrole-1,4-dione 2d

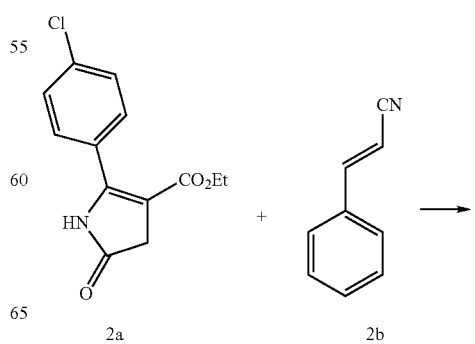

-continued

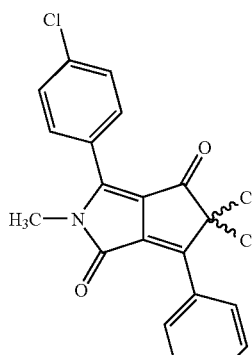

2d

To 2-methyl-2-butanol (300 ml) is added sodium (9.2 g, 0.400 mol) with stirring under nitrogen and the mixture is heated to reflux (105–110° C.) until all the sodium is dissolved. The mixture is cooled to 80° C. then compounds 2a (35.44 g, 0.133 mol) and 2b (17.22 g, 0.133 mol) are added. The mixture is heated to reflux for 16 h, then cooled slowly to room temperature. Methyl iodide (77.6 g, 0.547 mol) is added and the mixture is heated to 40° C. for 66 h. The mixture is cooled to room temperature and acidified slowly with dilute hydrochloric acid. The organic extracts are washed with water, dried (MgSO$_4$) and concentrated. Flash chromatography on silica gel H (Fluka, 5–40 μm particle size) eluted with hexane/ethyl acetate yields the fluorescent orange solid 2d (yield 6.49 g, 17%).

| Elemental analysis: | C | H | N | Cl |
|---|---|---|---|---|
| calculated | 70.5% | 4.0% | 7.5% | 9.5% |
| observed | 67.8% | 5.1% | 6.4% | 8.4% |

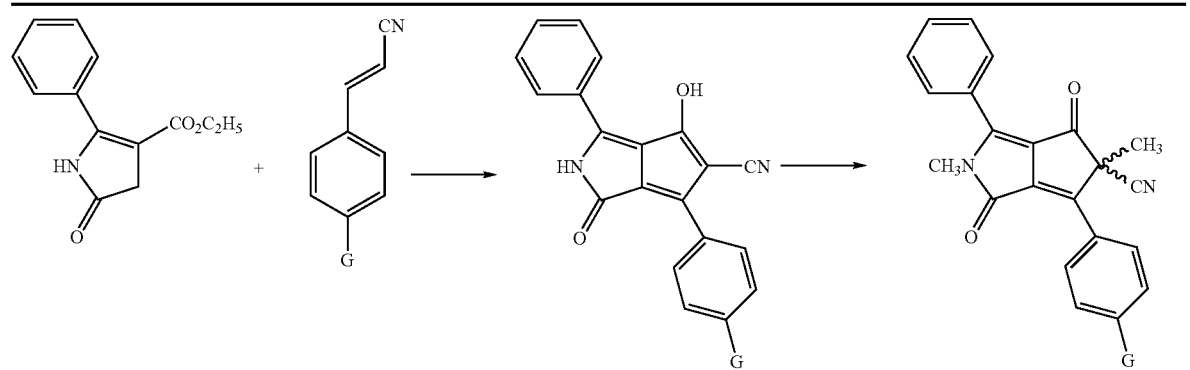

| 1a | 3b (G = CH$_3$) | 3c (G = CH$_3$) | 3d (G = CH$_3$) (Example 3) |
| 1a | 4b (G = Cl) | 4c (G = Cl) | 4d (G = Cl) (Example 4) |
| 1a | 5b (G = N(CH$_3$)$_2$) | 5c (G = N(CH$_3$)$_2$) | 5d (G = N(CH$_3$)$_2$) (Example 5) |
| 1a | 6b (G = OCH$_3$) | 6c (G = OCH$_3$) | 6d (G = OCH$_3$) (Example 6) |
| 1a | 7b (G = F) | 7c (G = F) | 7d (G = F) (Example 7) |

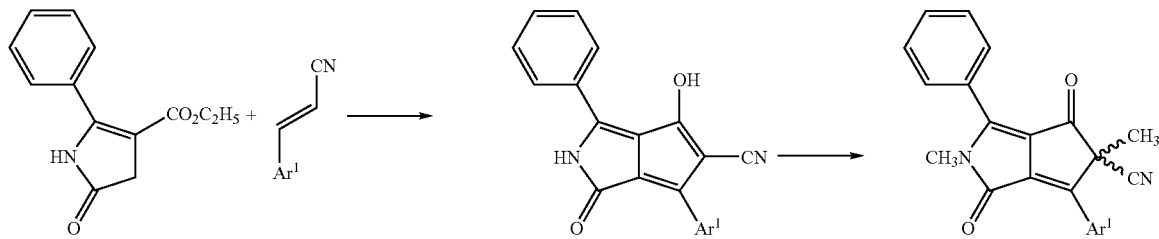

| 1a | 8b | 8c | 8d (Example 8) |

Ar$^1$ = 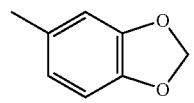

| 1a | 9b | 9c | 9d (Example 9) |

Ar$^1$ = 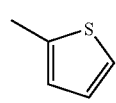

Example 3

5-Cyano-4-hydroxy-3-phenyl-6-(4-tolyl)-2H-cyclopenta[c]pyrrol-1-one 3c

To pre-dried t-amyl alcohol (150 ml) was added sodium (1.72 g, 0.0748 mol) with stirring under nitrogen and the mixture was heated to reflux (105–110° C.) until all the sodium dissolved. The lactam ester 1a (4.85 g, 0.0210 mol) was added, then nitrile 3b (3.0 g, 0.0210 mol) was added portionwise over 30 min during which time a dark red solution formed. Stirring was continued for 2 h at reflux, then for 15 h at 25° C. and the solution was added to an ice-cooled mixture of water (70 ml), methanol (10 ml) and concentrated hydrochloric acid (7.5 ml). The dark red solid was filtered off, washed with water then methanol and dried in vacuo. Yield 2.22 g (32%). (Found: C, 77.5; H, 4.4; N, 8.6. $C_{21}H_{14}N_2O_2$ requires C, 77.3; H, 4.3; N, 8.6%). v/cm$^{-1}$ 3114 (weak, N—H or O—H), 2209 (C≡N), 1668 (C=O). $\delta_H$ (DMSO-d$_6$) 2.37 (3H, s, CH$_3$), 7.31 (2H, d, J=8.2, H-3' and -5'), 7.55–7.57 (3H, m, H-3", -4" and -5"), 8.15 (2, dd, J 1.9 and 8.0, H-2' and -6'), 8.29–8.32 (2H, m, H-2" and -6"), 11.04 (1H, s, NH). In a manner similar to Example 3 the compounds 4c, 5c, 6c, 7c, 8c and 9c listed in the table were obtained:

| Example | Compound | Yield [%] | Mp. [° C.] | $^1$H-NMR |
|---|---|---|---|---|
| 4 | 4c | 54 | 290–292 | 7.51–7.58(5H, m, Ar-H), 8.25–8.28 (2H, m, Ar-H), 8.33–8.36(2H, m, Ar-H), 11.04(1H, s, NH) |
| 5 | 5c | 20 | — | 3.05(6H, s, N(CH$_3$)$_2$), 6.83–6.86(2H, m, Ar-H), 7.43–7.52(3H, m, Ar-H), 8.24–8.33(4H, m, Ar-H), 11.16(1H, s, NH) |
| 6 | 6c | 38 | 286–287 | 3.84(3H, s, OCH$_3$), 7.09(2H, d, J 9.0, o-Ar-H), 7.55–7.57(3H, m, Ar-H), 8.27–8.31(4H, m, Ar-H), 11.13(1H, s, NH) |
| 7 | 7c | 66 | 274–276 | 7.43(2H, t, J 9.0, Ar-H-3 an −5 in 4-FC$_6$H$_4$), 7.5(1H, Br s, OH), 7.55–7.70(3H, m, m-Ip-PhH), 8.51(2H, d, J 10.0, o-PhH), 8.51 [4H, coincident o-Ph(m) and Ar-H-2 and −6 in 4-FC$_6$H$_4$ (dd, J 9.0 and 5.6)], 10.73(1H, s, NH) |
| 8 | 8c | | 296–298 | 6.21(3H, s, CH2O2), 7.14(1H, d, J 8.2, H-5'), 7.58–7.66(4H, m, m- and p-Ph-H and OH), 8.07(1H, dd, j 8.2 and 1.8, H-6'), 8.14(1H, d, J 1.8, H-2'), 8.46(2H, d, J 8.9, o-Ph-H), 10.80 (1H, s, NH) |
| 9 | 9c | | 285–287 | 7.40(1H, dd, J 5.0 and 3.8, Th-H-4), 7.45–7.80(3H, m- and p-Ph-H), 7.97 (1H, d, J 4.6, Th-H-5), 8.2–8.6(2H, br, o-Ph-H), 8.74(1H, d, J 3.7, Th-H-3), 11.13(1H, s, NH) |

Example 10

5-Cyano-5-methyl-3,6-diphenyl-cyclopenta[c]pyrrole-1,4-dione 10

Example 1 was repeated, except that after the addition of methyl iodide heating was continued at 40° C. for 1 h. After recrystallisation from a propan-2-ol/tetrahydrofuran mixture 0.76 g (27%) of a fluorescent orange solid were obtained; m.p. 299–301° C. (Found: C, 77.3; H, 4.4; N, 8.4%. $C_{21}H_{14}N_2O_2$ requires C, 77.3, H, 4.3; N, 8.6%). v/cm$^{-1}$ 3167 (NH), 2365 (C≡N), 1677 (C=O), 1607. $\delta_H$ 1.90 (3H, s, CCH$_3$), 7.57–7.65 (6H, m, m-/p- Ar—H), 8.41–8.51 (4H, m, o- Ar—H), 12.22 (1H, s, NH) with trace impurity at 3.32 (<<1H, s, NCH$_3$). m/z 326 (M$^{+\cdot}$, 100%) with trace amount of product at 340.

Example 11

2-t-Butoxycarbonyl-5-cyano-4-hydroxy-3-(4'-methoxyphenyl)-6-phenyl-cyclopenta[c]pyrrol-1-one 11c

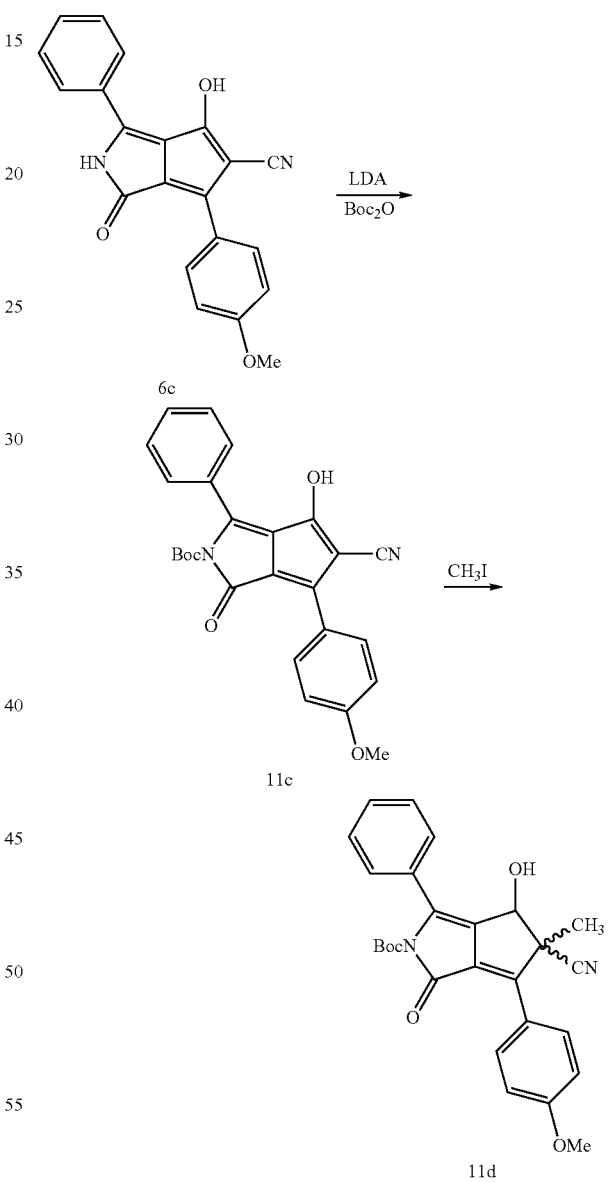

A solution of n-butyllithium in hexanes (1 M, 1.0 ml, 0.0025 mol) was added with stirring, under nitrogen, to a flask charged with tetrahydrofuran (25 ml) and diisopropylamine (0.42 g, 0.0042 mol) and stirring continued for 1.5 h. The solution was cooled to −78° C., then added dropwise to a mixture of derivative 6c and tetrahydrofuran (20 ml) at −78° C. under nitrogen. This purple coloured solution was stirred at −78° C. for 30 min., then Boc$_2$O (0.41 g, 0.0018 mol) was added in tetrahydrofuran (1.5 ml). The mixture was left to warm to 25° C. during 1 h then heated to reflux (65° C.) for 45 min. Further Boc$_2$O (0.71 g, 0.0033 mol) then DMAP (0.09 g, 0.0007 mol) were added and stirring continued for 20 h. Saturated aqueous ammonium chloride solution (6 ml) was then added, the mixture acidified to pH 6–7 with 10% hydrochloric acid, extracted with diethyl ether, dried over sodium sulfate then concentrated to dryness. Flash chromatography on silica gel H eluted with petrol/ethyl acetate (1:1), then methanol yielded a purple solid, which was dried in vacuo. Yield 0.16 g (28%). The product decomposed without melting. $\delta_H$ (200 MHz, DMSO-d$_6$), 1.25 [9H, s, O(CH$_3$)$_3$], 3.83 (3H, s, OCH$_3$), 7.01–7.06 (2H, m, Ar—H), 7.37–7.49 (3H, m, Ar—H), 7.62–7.68 (2H, m, Ar—H), 8.33–8.38 (2H, m, Ar—H). v/cm$^{-1}$ 2190 (C≡N), 1716 (C=O), 1644, 1606.

The intermediates 3c, 4c, 5c, 6c, 7c, 8c and 9c could be easily converted to the inventive compounds 3d, 4d, 5d, 6d, 7d, 8d and 9d by reacting them with sodium $^t$amyl alcoholate/$^t$amyl alcohol and methyl iodide.

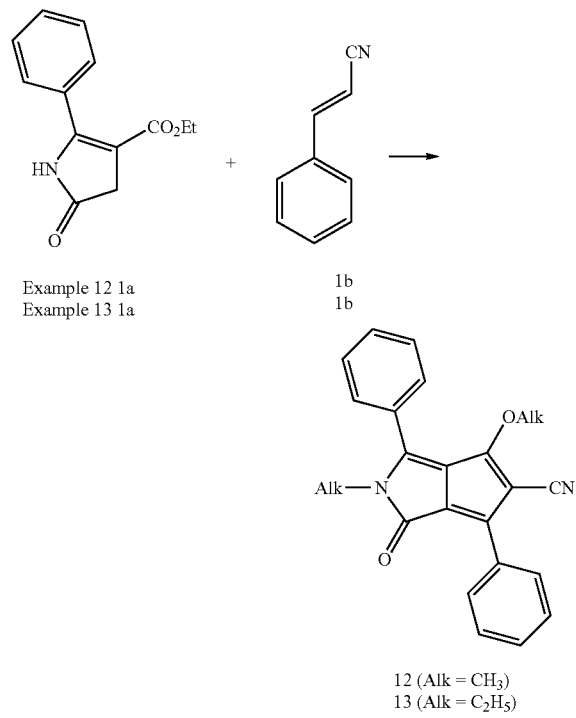

Example 12 1a
Example 13 1a
1b
1b 12 (Alk = CH$_3$)
13 (Alk = C$_2$H$_5$)

Example 12

5-Cyano-4-methoxy-N-methyl-3,6-diphenylcyclopenta[c]pyrrol-1-one 12

To pre-dried t-amyl alcohol (50 ml) was added sodium (1.22 g, 0.0531 mol) with stirring under nitrogen and the mixture was heated to reflux (105–110° C.) until all the sodium dissolved. The lactam ester 1a (4.0 g, 0.0173 mol) then cinnamonitrile 1b (4.46 g, 0.0345 mol) were added and heating to reflux continued for 4.5 h during which time a purple-red coloured solution developed. The mixture was cooled to 25° C., then methyl tosylate (25.22 g, 0.1354 mol) was added. Heating to reflux was continued for 1 h. The mixture was cooled, added to water (100 ml), extracted with ethyl acetate, dried (Na$_2$SO$_4$) then concentrated. The residue obtained was dissolved in sodium ethoxide/ethanol solution overnight and reprecipitated by addition to water and acidification with concentrated hydrochloric acid dropwise. Recrystallisation from propan-2-ol/tetrahydrofuran yielded a red-orange solid (1.22 g, 21%); m.p. 210–212° C. (Found: C, 77.3; H, 4.7; N, 8.2. C$_{22}$H$_{16}$N$_2$O$_2$ requires C, 77.6; H, 4.7, N, 8.2%). $\delta_H$ 3.18 (3H, s, NCH$_3$), 4.21 (3H, s, OCH$_3$), 7.43–7.66 (8H, m, Ar—H), 8.22 (2H, d, J 6.6, Ar—H). v/cm$^{-1}$ 2197 (C≡N), 1703 (C=O), 1677.

Example 13

5-Cyano4-ethoxy-N-ethyl-3,6-diphenylcyclopenta[c]pyrrol-1-one 13

Example 12 was repeated except that ethyl tosylate was used instead of methyl tosylate. 3.07 g (13%) of a red-orange product were obtained; m.p. 200–202° C. (Found: C, 78.0; H, 5.2; N, 7.8%. C$_{24}$H$_{20}$N$_2$O$_2$ requires C, 78.2, H, 5.5; N, 7.6%). v/cm$^{-1}$ 2195 (C≡N), 1694 (C=O), 1655. $\delta_H$ (200 MHz) 1.19 (3H, t, J 7.1, CH$_2$CH$_3$), 1.29 (3H, t, CH$_2$CH$_3$), 3.68 (2H, q, NCH$_2$CH$_3$), 4.55 (2H, q, OCH$_2$CH$_3$), 7.42–7.67 (8H, m, Ar—H), 8.22 (2H, dd, J 2.2 and 8.2, o-Ar—H).

Example 14

5-Cyano-4-methoxy-6-(p-methoxyphenyl)-N-methyl-3-phenylcyclopenta[c]pyrrol-1-one 13

Example 12 was repeated except that 6b was used instead of 1b. Yield 24%; m.p. 253–255° C. (Found: C, 74.7; H, 4.9; N, 7.7%. C$_{23}$H$_{18}$N$_2$O$_3$ requires C, 74.6, H, 4.9; N, 7.7%). v/cm$^{-1}$ 2200 (C≡N), 1701 (C=O), 1655. $\delta_H$ 3.19 (3H, s, NCH$_3$), 3.88 (3H, s, ArOCH$_3$), 7,00 (2H, d, J 8.8, H-3 and -5 in 4-MeOC$_6$H$_4$), 7.54–7.62 (5H, m, Ph—H), 8.33 (2H, d, J 8.8, H-2 and -6 in 4-MeOC$_6$H$_4$).

Example 15

1.0 g of the DPP analogue 1d or 2d was mixed with 63.0 g of polyvinyl chloride, 3.0 g of epoxidized soya oil, 2.0 g of barium/cadmium thermal stabilizer and 32.0 g of dioctyl phthalate, and the mixture was processed on a roller mill at 160° C. for 8 minutes to give a thin sheet. The PVC sheet thus produced is characterized by its very strong fluorescent yellow-orange colour.

The invention claimed is:

1. A fluorescent diketopyrrolopyrrole analogue of the formula

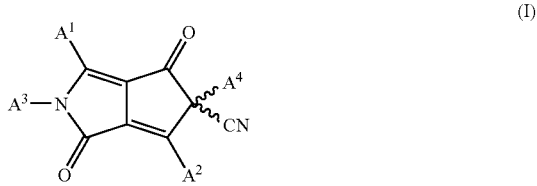

(I)

wherein A$^1$ and A$^2$ are C$_1$–C$_{18}$alkyl, C$_2$–C$_{18}$alkenyl, C$_2$–C$_{18}$alkynyl, C$_5$–C$_8$cycloalkyl, C$_5$–C$_8$cycloalkenyl, aryl or heteroaryl, A$^3$ and A$^4$ are independently of each other C$_1$–C$_{18}$alkyl, Ar$^3$, —CR$^{30}$R$^{31}$—(CH$_2$)$_m$—Ar$^3$, or Y—R$^{32}$, wherein R$^{30}$ and R$^{31}$ independently of each other stand for hydrogen or $C_1$–$C_4$alkyl, or phenyl which can be substituted up to three times with $C_1$–$C_3$alkyl, $Ar^3$ stands for aryl, $C_5$–$C_8$cycloalkyl, or heteroaryl, which can be substituted one to three times with $C_1$–$C_8$alkyl, $C_1$–$C_8$alkoxy, halogen or phenyl, which can be substituted with $C_1$–$C_8$alkyl or $C_1$–$C_8$alkoxy one to three times, and m stands for 0, 1, 2, 3 or 4, Y is —C(O)— or —$SO_2$— and $R^{32}$ is $C_1$–$C_{18}$alkyl, $Ar^3$, or aralkyl and $A^3$ can additionally be hydrogen, $C_1$–$C_8$alkyloxycarbonyl, or aralkyloxycarbonyl.

2. The diketopyrrolopyrrole analogue according to claim 1, wherein $A^1$ and $A^2$ are aryl or heteroaryl of the formula

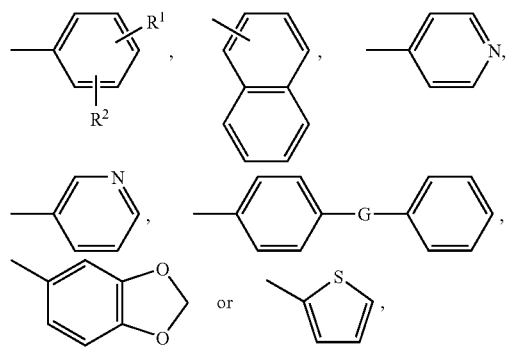

wherein $R^1$ and $R^2$ are independently of each other hydrogen, fluoro, chloro, bromo, $C_1$–$C_4$alkyl, $C_1$–$C_6$alkoxy, amino, $C_1$–$C_6$alkylamino, di($C_1$–$C_6$alkyl)amino, phenyl or CN, G is —O—, —$NR^7$—, —N=N— or —$SO_2$—, and $R^7$ is hydrogen, methyl or ethyl.

3. The diketopyrrolopyrrole analogue according to claim 1, wherein $A^1$ and $A^2$ are aryl of the formula

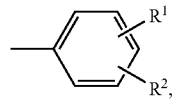

wherein $R^1$ and $R^2$ are independently of each other hydrogen, methyl, tert-butyl, fluoro, chloro, bromo, dimethylamino, phenyl or CN.

4. The diketopyrrolopyrrole analogue according to claim 1, wherein $A^3$ is $C_1$–$C_8$alkyl, Y—$R^{32}$ wherein Y is —C(O)— and $R^{32}$ is

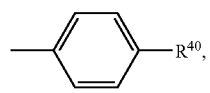

wherein $R^{40}$ is hydrogen, $C_1$–$C_4$alkyl, —O—$C_1$–$C_4$alkyl, —S—$C_1$–$C_4$alkyl or —$(CH_2)_m$—Ar wherein m is 0 or 1 and Ar is a group of the formula

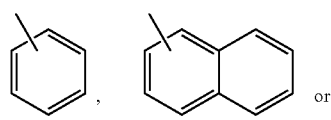

-continued

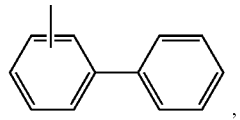

which can be substituted one to three times with $C_1$–$C_8$alkyl, $C_1$–$C_8$alkoxy, halogen or phenyl.

5. The diketopyrrolopyrrole analogue according to claim 1, wherein $A^4$ is $C_1$–$C_8$alkyl, Y—$R^{32}$ wherein Y is —C(O)— and $R^{32}$ is

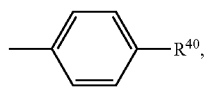

wherein $R^{40}$ is hydrogen, $C_1$–$C_4$alkyl, —O—$C_1$–$C_4$alkyl, —S—$C_1$–$C_4$alkyl or —$(CH_2)_m$—Ar wherein m is 0 or 1 and Ar is a group of the formula

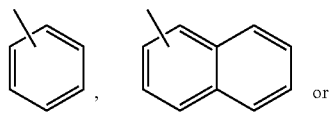

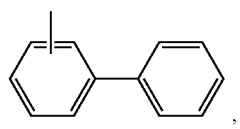

which can be substituted one to three times with $C_1$–$C_8$alkyl, $C_1$–$C_8$alkoxy, halogen or phenyl.

6. A process for the preparation of the fluorescent diketopyrrolopyrrole analogue of the formula I according to claim 1, comprising reacting a compound of the formula

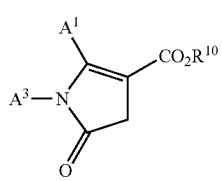

(II)

with a compound of the formula

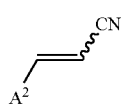

(III)

in the presence of a base and reacting the obtained intermediate of the formula

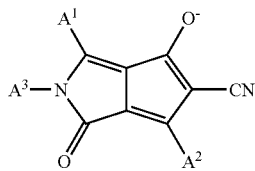

(IV')

with a compound of the formula

A⁴—X   (V), wherein $A^1$, $A^2$, $A^3$ and $A^4$ have the meanings as given in claim 1, $R^{10}$ is $C_1$–$C_{18}$alkyl, aryl, or aralkyl, which can be substituted one to three times with $C_1$–$C_8$alkyl, $C_1$–$C_8$alkoxy or halogen, and X is a leaving group.

7. A composition comprising
(a) 0.01 to 50% by weight, based on the total weight of the coloured high molecular weight organic material, of the diketopyrrolopyrrole analogue of formula I according to claim 1, and
(b) 99.99 to 50% by weight, based on the total weight of the coloured high molecular weight organic material, of a high molecular organic material, and
(c) optionally, customary additives in effective amounts.

8. A method of colouring a high molecular weight organic material by incorporating therein a diketopyrrolopyrrole analogue of formula I according to claim 1.

9. A process for coloring inks, colourants, pigmented plastics for coatings, non-impact-printing material, colour filters, cosmetics, polymeric ink particles or toners by adding the diketopyrrolopyrrole analogue of formula I according to claim 1.

10. A diketopyrrolopyrrole analogue of the general formula

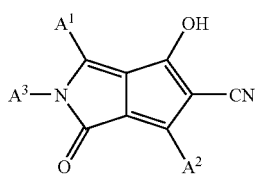

(IV)

wherein $A^1$, $A^2$ and $A^3$ have the meanings as given in claim 1.

11. A fluorescent diketopyrrolopyrrole analogue according to claim 1 of the formula

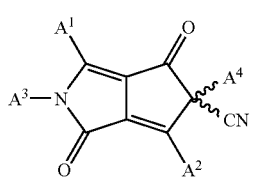

(I)

wherein the aryl or heteroaryl of $A^1$ and $R^2$ are defined independently of each other as radicals of the formula

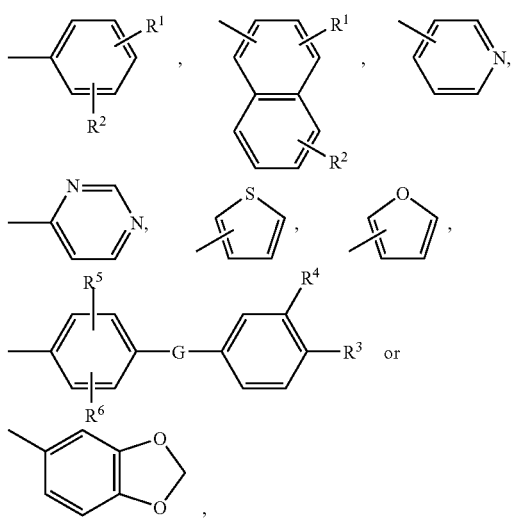

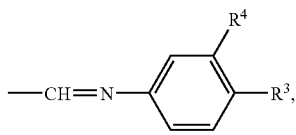

wherein
$R^1$ and $R^2$ are independently of each other hydrogen, halogen, $C_1$–$C_{18}$alkyl, $C_1$–$C_{18}$alkoxy, $C_1$–$C_{18}$alkylmercapto, amino, $C_1$–$C_{18}$alkylamino, di($C_1$–$C_{18}$alkyl)amino, $C_1$–$C_{18}$alkoxycarbonyl, $C_1$–$C_{18}$alkylaminocarbonyl, —CN, —NO₂, trifluoromethyl, $C_5$–$C_8$cycloalkyl, —CH=N—($C_1$–$C_{18}$alkyl), imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl,
G is —CH₂—, —CH(CH₃)—, —C(CH₃)₂—, —CH=N—, —N=N—, —O—, —S—, —SO—, —SO₂—, —CONH— or —NR⁷—,
$R^3$ and $R^4$ are independently of each other hydrogen, halogen, $C_1$–$C_6$alkyl, $C_1$–$C_{18}$alkoxy or —CN,
$R^5$ and $R^6$ are independently of each other hydrogen, halogen or $C_1$–$C_6$alkyl, and $R^7$ is hydrogen or $C_1$–$C_6$alkyl, and $A^3$ and $A^4$ are defined as in claim 1.

12. A dye laser or electroluminescent composition comprising the diketopyrrolopyrrole analogue of formula I according to claim 1.

13. A fluorescent marker composition for immunoassays and fluorescent tracers for leak detection of fluids comprising the diketopyrrolopyrrole analogue of formula I according to claim 1.

14. A composition comprising
(a) 0.01 to 50% by weight, based on the total weight of the coloured high molecular weight organic material, of the diketopyrrolopyrrole analogue of formula I according to claim 11, and
(b) 99.99 to 50% by weight, based on the total weight of the coloured high molecular weight organic material, of a high molecular organic material, and
(c) optionally, customary additives in effective amounts.

15. A method of colouring a high molecular weight organic material by incorporating therein a diketopyrrolopyrrole analogue of formula I according to claim 11.

16. A process for coloring inks, colourants, pigmented plastics for coatings, non-impact-printing material, colour filters, cosmetics, polymeric ink particles or toners by adding the diketopyrrolopyrrole analogue of formula I according to claim 11.

17. A dye laser or electroluminescent composition comprising the diketopyrrolopyrrole analogue of formula I according to claim 11.

18. A fluorescent marker composition for immunoassays and fluorescent tracers for leak detection of fluids comprising the diketopyrrolopyrrole analogue of formula I according to claim 11.

* * * * *